(12) United States Patent
Belson

(10) Patent No.: US 8,114,114 B2
(45) Date of Patent: Feb. 14, 2012

(54) EMBOLIC PROTECTION DEVICE

(75) Inventor: Amir Belson, Cupertino, CA (US)

(73) Assignee: Emboline, Inc., Los Altos, CA (US)

( * ) Notice: Subject to any disclaimer, the term of this patent is extended or adjusted under 35 U.S.C. 154(b) by 1062 days.

(21) Appl. No.: 10/493,854

(22) PCT Filed: Aug. 27, 2003

(86) PCT No.: PCT/US03/26938
§ 371 (c)(1),
(2), (4) Date: Apr. 27, 2004

(87) PCT Pub. No.: WO2004/019817
PCT Pub. Date: Mar. 11, 2004

(65) Prior Publication Data
US 2004/0215167 A1 Oct. 28, 2004

Related U.S. Application Data

(60) Provisional application No. 60/406,492, filed on Aug. 27, 2002.

(51) Int. Cl.
*A61M 29/00* (2006.01)
(52) U.S. Cl. ................... 606/200
(58) Field of Classification Search .......... 606/200, 606/151, 157, 213; 623/1.11
See application file for complete search history.

(56) References Cited

U.S. PATENT DOCUMENTS

| | | | | |
|---|---|---|---|---|
| 4,723,549 A * | 2/1988 | Wholey et al. | ...... | 606/194 |
| 4,790,809 A * | 12/1988 | Kuntz | ........... | 604/8 |
| 5,108,419 A * | 4/1992 | Reger et al. | ........ | 606/200 |
| 5,800,525 A * | 9/1998 | Bachinski et al. | ... | 623/1.1 |
| 6,117,154 A * | 9/2000 | Barbut et al. | ....... | 606/181 |
| 6,348,063 B1 * | 2/2002 | Yassour et al. | ...... | 606/200 |
| 6,361,545 B1 * | 3/2002 | Macoviak et al. | .. | 606/200 |
| 6,461,370 B1 * | 10/2002 | Gray et al. | ........... | 606/200 |
| 6,746,469 B2 * | 6/2004 | Mouw | ................. | 606/200 |
| 7,758,606 B2 * | 7/2010 | Streeter et al. | ....... | 606/200 |

* cited by examiner

*Primary Examiner* — Darwin Erezo
*Assistant Examiner* — Gregory Anderson
(74) *Attorney, Agent, or Firm* — Wilson Sonsini Goodrich & Rosati

(57) ABSTRACT

The embolic protection device (10) has an expandable tubular structure supporting a filter mesh material (12). The embolic protection device is compressed to a small diameter for insertion into a patient's aorta, then expanded within the aorta with the filter mesh material positioned to allow blood to enter sidebranch vessels connected to the aorta and to prevent embolic material from entering the sidebranch vessels. The filter mesh material may be configured with waves or undulations (26) for increased surface area and/or with two layers of mesh material to provide additional protection against embolization and to prevent inadvertent occlusion of the sidebranch vessels.

35 Claims, 5 Drawing Sheets

EMBOLIC PROTECTION DEVICE

CROSS REFERENCE TO OTHER APPLICATIONS

The present application claims priority of U.S. Provisional Patent Application 60/406,492, filed on Aug. 27, 2002.

FIELD OF THE INVENTION

The present invention relates to apparatus and methods for providing embolic protection to a patient's aortic arch vessels during cardiac surgery and interventional cardiology procedures.

BACKGROUND OF THE INVENTION

Cerebral embolism is a known complication of cardiac surgery, cardiopulmonary bypass and catheter-based interventional cardiology and electrophysiology procedures. Embolic particles, which may include thrombus, atheroma and lipids, may become dislodged by surgical or catheter manipulations and enter the bloodstream, embolizing in the brain or other vital organs downstream. Cerebral embolism can lead to neuropsychological deficits, stroke and even death. Prevention of cerebral embolism would benefit patients and improve the outcome of these procedures.

Previous devices for preventing cerebral embolism are described in the following U.S. patents and patent applications, which are hereby incorporated by reference: U.S. Pat. No. 6,371,935 Aortic catheter with flow divider and methods for preventing cerebral embolization, U.S. Pat. No. 6,361,545 Perfusion filter catheter, U.S. Pat. No. 6,254,563 Perfusion shunt apparatus and method, U.S. Pat. No. 6,139,517 Perfusion shunt apparatus and method, U.S. Pat. No. 6,537,297 Methods of protecting a patient from embolization during surgery, U.S. Pat. No. 6,499,487 Implantable cerebral protection device and methods of use, U.S. Pat. No. 5,769,816 Cannula with associated filter, US20030100940A1 Implantable intraluminal protector device and method of using same for stabilizing atheromas.

SUMMARY OF THE INVENTION

The present invention takes the form of apparatus and methods for providing embolic protection to a patient's aortic arch vessels during cardiac surgery and interventional cardiology and electrophysiology procedures. Embolic particles in the aortic blood flow are prevented from entering the aortic arch vessels and carotid arteries that lead to the brain. The apparatus and methods of the present invention can also be used for embolic protection of other organ systems, such as the renal system.

In one embodiment, a stent-like embolic protection device is constructed of a self-expanding tubular mesh that may be woven out of wires or fibers or formed from a tube or sheet. The embolic protection device is compressed to a small diameter and inserted into a delivery tube or catheter, which is introduced via a peripheral artery or an aortotomy and advanced into the aortic arch. Once in place, the delivery tube is withdrawn to allow the device to expand similar to a self-expanding stent. The mesh of the device covers the ostia of the arch vessels, allowing blood to enter, but preventing potential emboli from entering the aortic arch vessels and carotid arteries. The device conforms closely to the walls of the aorta so that it will not interfere with performing cardiac surgery or interventional cardiology procedures. The embolic protection device may be collapsed and withdrawn from the aorta after the procedure or it may be left in the aorta for long-term embolic protection.

In another embodiment, the embolic protection device may be made with a flat panel of fine mesh textile fabric that is supported on a wire frame or the like. The panel of fine mesh fabric is held in place over the aortic arch vessels by the wire frame to filter out potential emboli. Being made of fabric, the device is free to conform to the ostia of the arch vessels to allow more surface area for blood flow compared to a flat panel. The wire frame may be attached to a handle or cannula for insertion through an aortotomy or to a catheter for peripheral artery insertion. In addition, the wire frame may include one or more wire hoops or a stent-like tubular structure for supporting the embolic protection device within the aortic arch.

Additional features are described which may be used with either embodiment of the embolic protection device. An embolic protection device is described with waves or undulations to provide more surface area for filtering out potential emboli and to prevent inadvertent occlusion of the arch vessels. Another embolic protection device is described with two layers of mesh material to provide additional protection against embolization and to prevent inadvertent occlusion of the arch vessels. An embolic protection device is described with an inflatable toroidal balloon for supporting the filter mesh material within the aorta. The embolic protection device or a portion of it may be coated with an antithrombogenic coating to reduce the formation of clots that could become potential emboli.

DETAILED DESCRIPTION OF THE INVENTION

Figure 1:
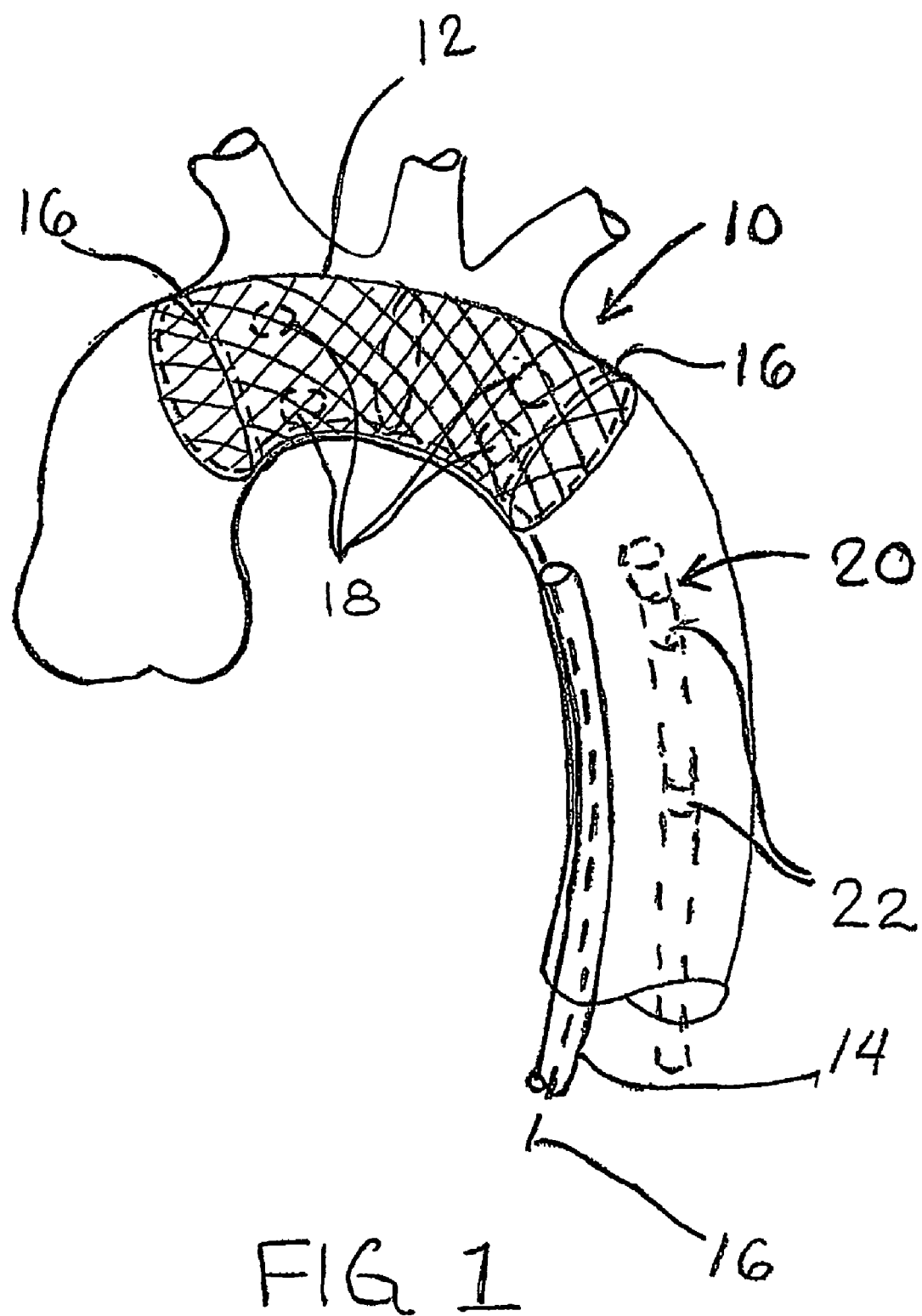
FIG. 1 shows a stent-like embolic protection device deployed within a patient's aortic arch for protecting the aortic arch vessels and carotid arteries from potential emboli.

FIG. 1 shows a stent-like embolic protection device 10 deployed within a patient's aortic arch for protecting the aortic arch vessels and carotid arteries from potential emboli. The embolic protection device 10 is made of a resilient material, either a polymer or a metal (e.g. Nitinol) or a combination of materials. The device 10 may be woven out of wires or fibers to form a tubular mesh structure 12 or by slitting and expanding a tube or sheet. Alternatively, the device 10 may be constructed with a tubular mesh structure 12 made of a flexible textile mesh with one or more wire hoops or a stent-like tubular structure for supporting the tubular mesh structure 12 within the aortic arch. The device 10 is compressible to a small diameter for insertion into the aorta via peripheral artery access or through an aortotomy. The device 10 is preferably self-expanding and, when expanded, has a generally tubular shape that conforms to the diameter and curvature of the aortic arch.

The embolic protection device 10 is compressed to a small diameter and inserted into a delivery tube or catheter 14. The delivery tube is introduced via a peripheral artery or an aortotomy and advanced into the aortic arch. Once in place, the delivery tube 14 is withdrawn to allow the device 10 to expand similar to a self-expanding stent. The mesh 12 of the device covers the ostia of the arch vessels, allowing blood to enter, but preventing potential emboli from entering the aortic arch vessels and carotid arteries. The device 10 conforms closely to the walls of the aorta so that it will not interfere with performing cardiac surgery or catheter-based interventional cardiology or electrophysiology procedures.

Alternatively, the embolic protection device 10 may be balloon-expandable. In this case, the embolic protection device 10 would be crimped or compressed onto an expandable balloon mounted on a catheter. The catheter is introduced into the aortic arch and the balloon is expanded to deploy the embolic protection device 10 in the aorta. Other volume expanding mechanisms, such as a mechanical expander, may be used in lieu of an expandable balloon.

After the procedure is completed, the embolic protection device 10 may be compressed and withdrawn from the aorta. Alternatively, the device 10 may be left in the aorta for long-term embolic protection. The device 10 may be compressed using one or more drawstrings 16 that encircle the device. The drawstrings 16 are pulled to compress the device and the device is withdrawn into the delivery tube 14 for removal. Alternatively, the embolic protection device 10 may be stretched longitudinal with the aid of a catheter, which will cause the diameter of the device to contract. Alternatively, the embolic protection device 10 may use a magnetic mechanism for compressing the device for removal. Multiple magnets 18 are arranged around the periphery of the device 10. After the procedure is completed, a catheter 20 carrying one or more strong magnets 22 is inserted through the lumen of the device 10 to compress the device around the catheter for removal.

Figure 2:
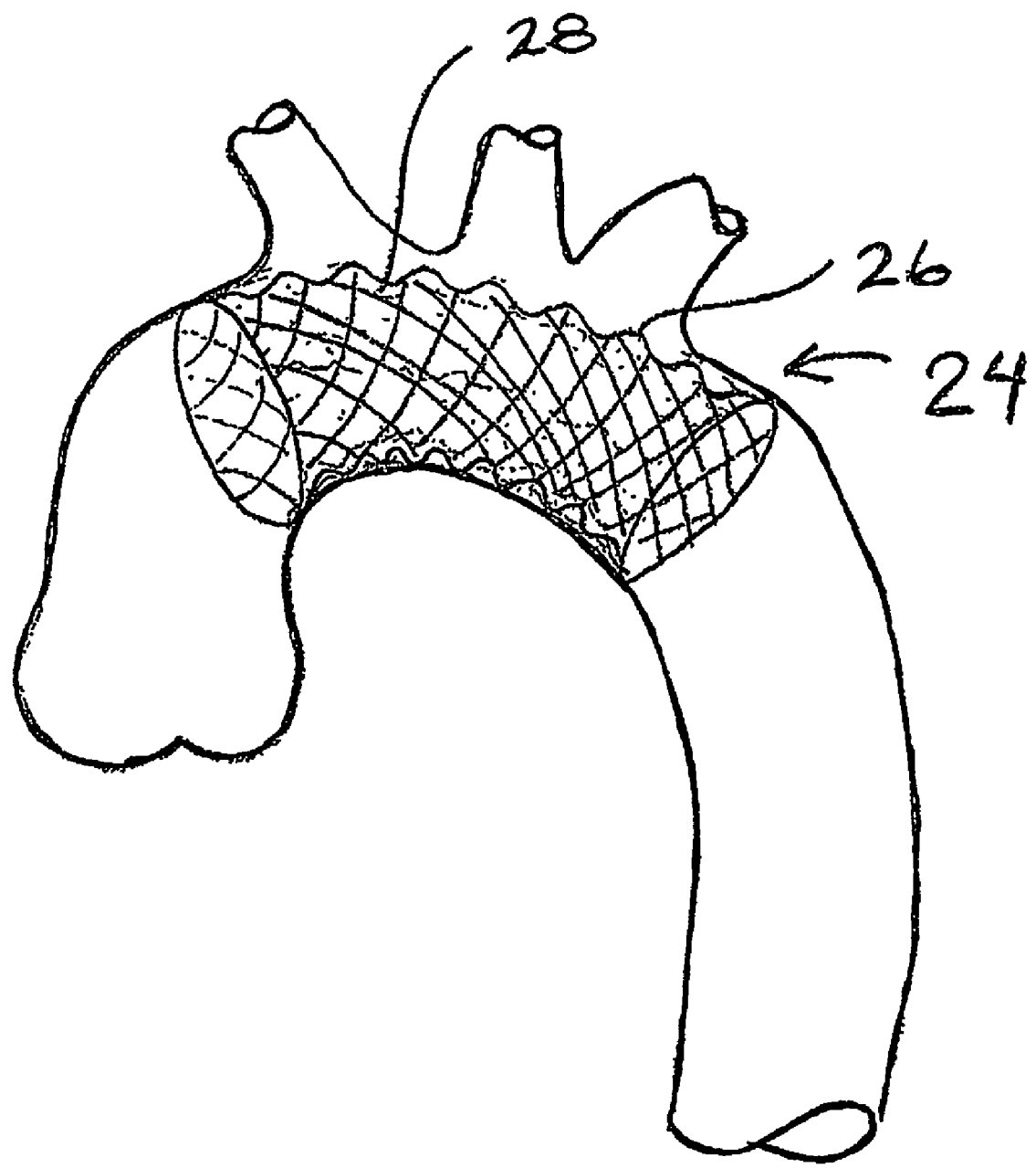
FIG. 2 shows a stent-like embolic protection device with waves or undulations.

FIG. 2 shows a stent-like embolic protection device 24 with waves or undulations 26 in the tubular mesh structure 28. The waves or undulations 26 in the embolic protection device 24 provide more surface area for filtering out potential emboli and prevents inadvertent occlusion of the arch vessels. This feature may be combined with any of the other embodiments and features of the invention described herein.

Figure 3:
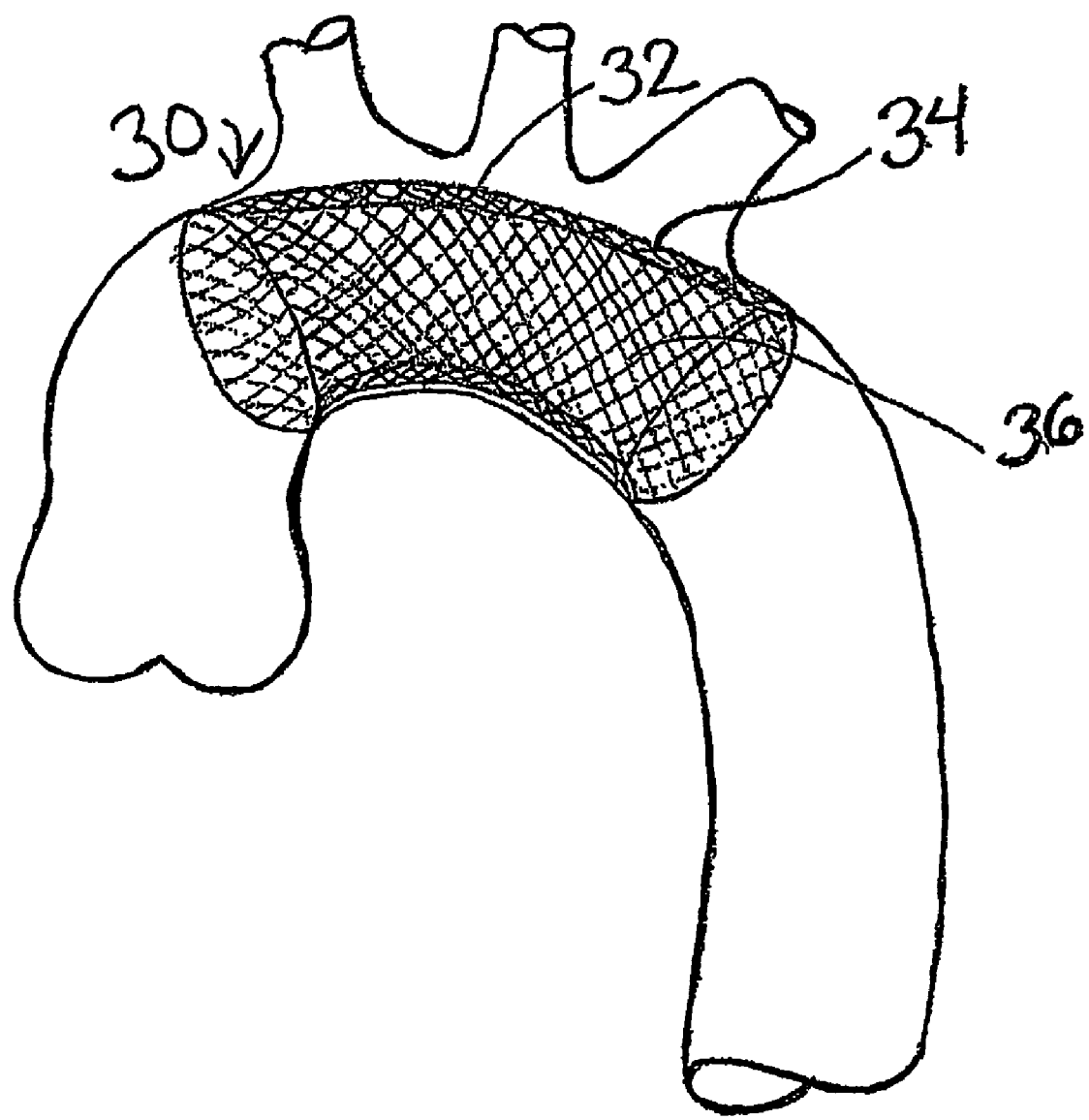
FIG. 3 shows a cut-away view of a stent-like embolic protection device with two layers of mesh material.

FIG. 3 shows a cut-away view of a stent-like embolic protection device 30 wherein the tubular mesh structure 32 is constructed with two layers of mesh material. The embolic protection device 30 preferably has an outer layer 34 of fine mesh material and an inner layer 36 of coarse mesh material. The outer layer 34 is shown cut away so that the inner layer 36 is visible. One or both layers of the device 30 may be self-expanding. For example, the outer layer 34 may be made of a fine mesh textile fabric, while the inner layer 36 is made with a self-expanding wire mesh structure. The two-layer structure provides additional protection against embolization and prevents the fine mesh of the outer layer 34 from becoming clogged with large emboli. Also, because blood can flow between the inner and outer layers of the device, all of the arch vessels will continue to receive blood flow even if the inner layer in front of one or more of the vessels becomes clogged. This feature may be combined with any of the other embodiments and features of the invention described herein. For example, one or both layers of the two-layer construction may be made with waves or undulations as described above in connection with FIG. 2.

Figure 4:
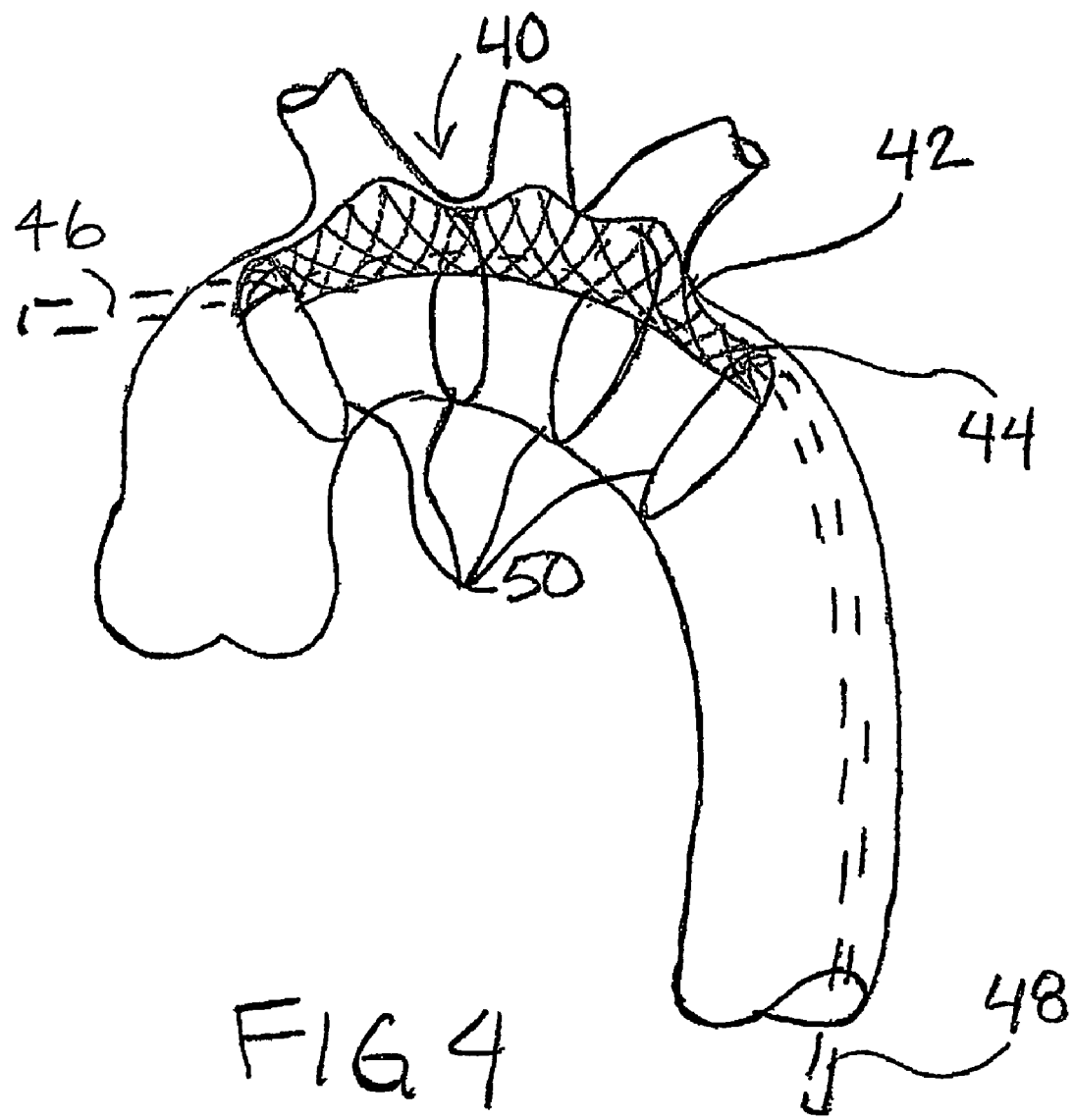
FIG. 4 shows an alternative embodiment of an embolic protection device.

FIG. 4 shows an alternative embodiment of an embolic protection device 40. In this embodiment, the embolic protection device 40 may be made with a panel of fine mesh textile fabric 42 that is supported on a wire frame 44 or the like. The panel of fine mesh fabric 42 is held in place over the aortic arch vessels by the wire frame 44 to filter out potential emboli. Being made of fabric, the mesh panel 42 is free to conform to the ostia of the arch vessels to allow more surface area for blood flow compared to a totally flat panel.

The wire frame 44 may be attached to a handle or cannula 46 for insertion through an aortotomy or to a catheter 48 for peripheral artery insertion. Alternatively or in addition, the wire frame 44 may include one or more wire hoops 50 in order to encircle the mesh panel or a stent-like tubular structure for supporting the embolic protection device 40 within the aortic Further, at least a portion of a wire hoop that extends away panel is not covered or directly attached to the mesh panel embodiment and/or its features may be combined with any of the other embodiments and features of the invention described herein. For example, the mesh panel 42 may be made with waves or undulations as described above in connection with FIG. 2 and/or with a two-layer construction as described in connection with FIG. 3. As a further example, the handle, cannula 46 or catheter 48 for insertion of the embolic protection device 40 described in connection with FIG. 4 may also be combined with any of the embolic protection devices described in connection with FIGS. 1-3 and 5.

Figure 5:
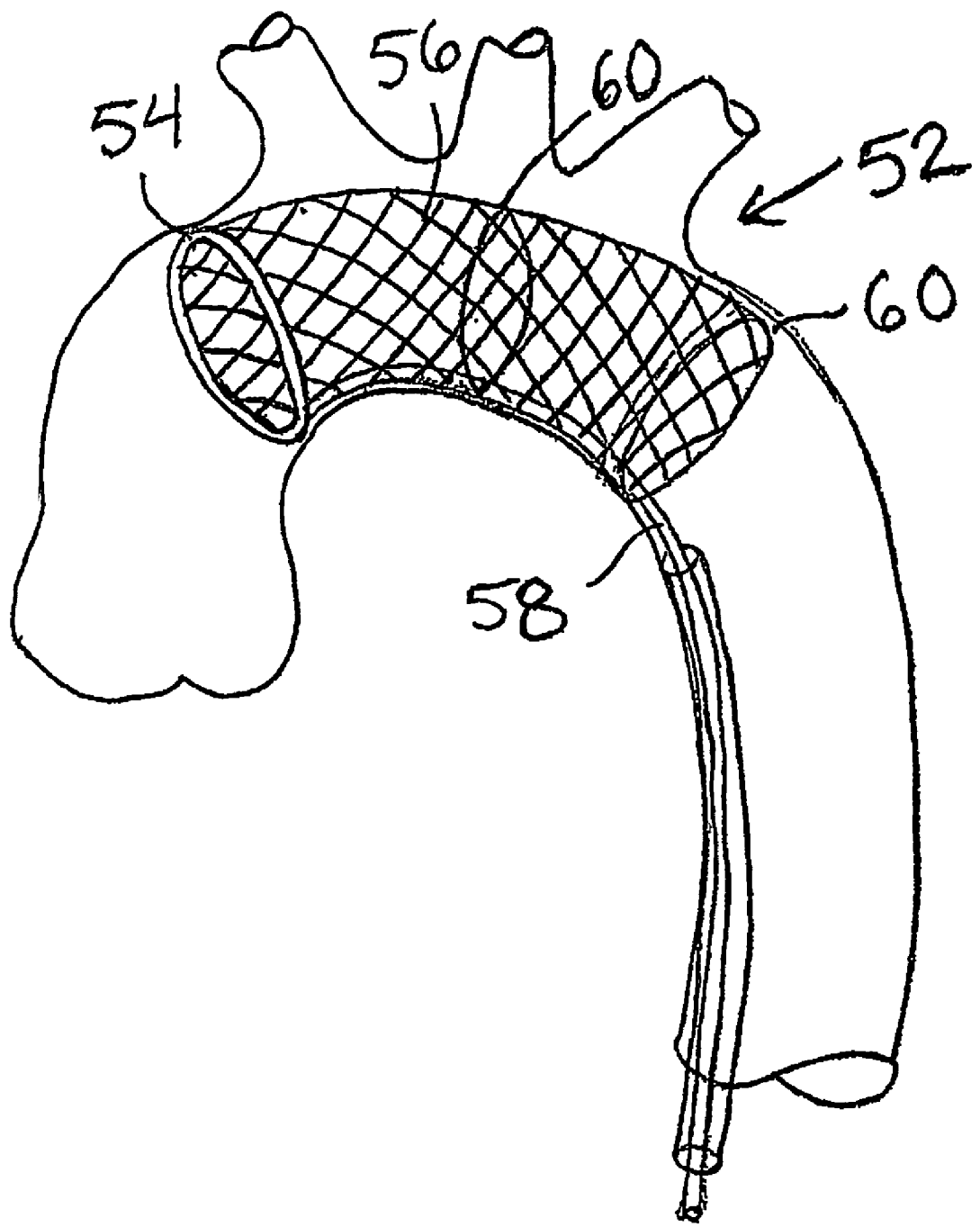
FIG. 5 shows another alternative embodiment of an embolic protection device.

FIG. 5 shows another alternative embodiment of an embolic protection device 52. An inflatable toroidal balloon 54 supports the upstream end of a tubular mesh structure 56. The toroidal balloon 54 is inflated and deflated through a catheter 58 having an inflation lumen and, optionally, a guidewire lumen. The tubular mesh structure 56 may be a self-expanding structure woven of wires or fibers or it may be a flexible textile mesh. Optionally, one or more wire hoops 60 or the like may be used to support the tubular mesh structure 56 within the patent's aorta. Alternatively, one or more additional inflatable toroidal balloons 54 may be used in place of the optional wire hoops 60 to support the tubular mesh structure 56. The features of this embodiment may be combined with any of the other embodiments and features of the invention described herein. For example, one or more inflatable toroidal balloons 54 may be combined with the embolic protection devices described in connection with FIGS. 1-3 for supporting a tubular mesh structure or panel of mesh material.

The entire embolic protection device or a portion of it may be coated with an antithrombogenic coating, for example a bonded heparin coating, to reduce the formation of clots that could become potential emboli. Alternatively or in addition, the embolic protection device or a portion of it may have a drug-eluting coating containing an anti-inflammatory or anti-stenosis agent.

The embolic protection device of the present invention can also be used for embolic protection of other organ systems. For example, an embolic protection device can be deployed in the patient's descending aorta for preventing embolic particles in the aortic blood flow from entering the renal arteries and embolizing in the patient's kidneys.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof.

What is claimed is:

1. An embolic protection device for deployment within a patient's aorta comprising: a substantially flat panel of filter mesh material supported on a wire frame, the wire frame encircling a periphery of the substantially flat panel of filter mesh material, the wire frame comprising at least one wire hoop configured for supporting the embolic protection device within the patient's aorta, the embolic protection device having a compressed position, wherein the embolic protection device is compressed to a small diameter for insertion into the patient's aorta, and an expanded position, wherein the embolic protection device expands to a larger size within the patient's aorta, wherein, when the embolic protection device is in the expanded position, the at least one wire hoop expands away from a plane of the flat panel of filter mesh material to a deployed position configured to support the wire frame and the panel of filter mesh material within the aorta such that the filter mesh material is adapted to cover ostia of sidebranch vessels connected to the patient's aorta and allow blood to enter the sidebranch vessels, but prevent embolic material from entering the sidebranch vessels, and wherein a portion of the at least one wire hoop extending away from the flat panel of filter mesh material is not covered by or directly attached to the filter mesh material.

2. The embolic protection device of claim 1, wherein the wire frame comprises a plurality of wire hoops, the wire hoops extending away from the plane of the flat panel of filter mesh material and supporting the embolic protection device within the patient's aorta when the embolic protection device is in the expanded position.

3. The embolic protection device of claim 1, wherein the wire frame supporting the panel of filter mesh material is a self-expanding structure.

4. The embolic protection device of claim 1, wherein the filter mesh material is configured with waves or undulations.

5. The embolic protection device of claim 1, wherein the panel of filter mesh material is configured with a first layer constructed of a fine mesh textile fabric and a second layer constructed of a self-expanding wire mesh structure.

6. The embolic protection device of claim 1, wherein the panel of filter mesh material is configured with a first layer of a coarse mesh material and a second layer of a fine mesh material.

7. The embolic protection device of claim 1, further comprising a delivery tube sized and configured to hold the embolic protection device in its compressed position.

8. The embolic protection device of claim 1, wherein the wire frame is attached to a catheter configured for peripheral artery insertion into the patient's aorta.

9. An embolic protection device for deployment within a patient's aorta comprising:
   an expandable tubular structure comprising a filter mesh material, the tubular structure having a compressed position, wherein the tubular structure is compressed to a small diameter for insertion into the patient's aorta, and an expanded position, wherein the tubular structure expands to a larger diameter that conforms to an inner wall of the patient's aorta, wherein, when the tubular structure is in the expanded position, the filter mesh material allows blood to enter sidebranch vessels connected to the patient's aorta, but prevents embolic material from entering the sidebranch vessels, and a plurality of magnets attached to the tubular structure and a magnetic retrieval catheter for collapsing the tubular structure and withdrawing the embolic protection device from the patient,
   wherein the plurality of magnets are arranged around a periphery of the tubular structure, such that, when the magnetic retrieval catheter is inserted into the tubular structure, the tubular structure collapses to a reduced diameter around the magnetic retrieval catheter.

10. The embolic protection device of claim 9, further comprising a drawstring encircling the tubular structure for selectively compressing the tubular structure to a small diameter for withdrawal from the patient.

11. The embolic protection device of claim 9, further comprising an inflatable toroidal balloon for supporting the expandable tubular structure.

12. The embolic protection device of claim 9, further comprising one or more wire hoops for supporting the expandable tubular structure.

13. The embolic protection device of claim 9, wherein the filter mesh material comprises an inner layer of filter mesh configured as a first tubular mesh structure and an outer layer of filter mesh configured as a second tubular mesh structure surrounding the first tubular mesh structure of the inner layer of filter mesh.

14. The embolic protection device of claim 13, further comprising a space between the first tubular mesh structure and the second tubular mesh structure to allow blood flow between the inner layer of filter mesh and the outer layer of filter mesh.

15. A method of providing embolic protection for sidebranch vessels connected to a patient's aorta comprising: introducing an embolic protection device into the patient's aorta, the embolic protection device comprising a wire frame supporting a substantially flat panel of filter mesh material, the wire frame encircling a periphery of the substantially flat panel of filter mesh material, the wire frame comprising at least one wire hoop configured for supporting the embolic protection device within the patient's aorta, the embolic protection device having a compressed position, wherein the embolic protection device is compressed to a small diameter for insertion into the patient's aorta; and expanding the embolic protection device to an expanded position within the patient's aorta, wherein, when the embolic protection device is in the expanded position, the at least one wire hoop expands away from a plane of the flat panel of filter mesh material to a deployed position configured to support the wire frame and the panel of filter mesh material within the aorta such that the filter mesh material covers ostia of the sidebranch vessels from the patient's aorta and allows blood to enter the sidebranch vessels, but prevents embolic material from entering the sidebranch vessels, wherein a portion of the at least one wire hoop extending away from the flat panel of filter mesh material is not covered by or directly attached to the filter mesh material.

16. The method of claim 15, wherein the filter mesh material is configured with waves or undulations.

17. The method of claim 15, wherein the panel of filter mesh material is configured with a first layer constructed of a fine mesh textile fabric and a second layer constructed of a self-expanding wire mesh structure.

18. The method of claim 15, wherein the panel of filter mesh material is configured with a first layer of a coarse mesh material and a second layer of a fine mesh material.

19. The method of claim 15, further comprising compressing the embolic protection device into a delivery tube for introduction of the embolic protection device into the aorta.

20. The method of claim 15, further comprising performing cardiac surgery or a catheter-based interventional cardiology or electrophysiology procedure on the patient while the embolic protection device is positioned within the aorta.

21. A method of providing embolic protection for sidebranch vessels connected to a patient's aorta comprising:
   introducing an embolic protection device into the patient's aorta, the embolic protection device comprising an expandable tubular structure supporting a filter mesh material, the tubular structure having a compressed position, wherein the tubular structure is compressed to a small diameter for insertion into the patient's aorta, and an expanded position, wherein the tubular structure expands to a larger diameter that conforms to an inner wall of the patient's aorta, wherein the embolic protection device further comprises a plurality of magnets attached to the tubular structure with the plurality of magnets arranged around a periphery of the tubular structure;

expanding the tubular structure within the patient's aorta such that the filter mesh material allows blood to enter the sidebranch vessels connected to the patient's aorta, but prevents embolic material from entering the sidebranch vessels;

inserting a magnetic retrieval catheter into the tubular structure to collapse the tubular structure to a reduced diameter around the magnetic retrieval catheter; and withdrawing the collapsed embolic protection device from the patient with the magnetic retrieval catheter.

22. The method of claim 21, wherein the embolic protection device further comprises a drawstring encircling the tubular structure for selectively compressing the tubular structure to a small diameter for withdrawal from the patient.

23. An embolic protection device for deployment within a patient's aorta comprising: an embolic filter attached to a catheter configured for peripheral artery insertion into the patient's aorta, the embolic filter comprising a substantially flat panel of flexible filter mesh material supported on a wire frame, the embolic protection device having a compressed position, wherein the embolic filter is compressed to a small diameter for insertion into the patient's aorta via peripheral artery insertion, and an expanded position, wherein the embolic filter expands to a larger size within the patient's aorta, wherein, when the embolic protection device is in the expanded position, the catheter supports the embolic filter within the aorta such that the flexible filter mesh material is configured to cover ostia of sidebranch vessels connected to the patient's aortic arch and allow blood to enter the sidebranch vessels, but prevent embolic material from entering the sidebranch vessels, wherein the panel of flexible filter mesh material is configured to conform to the patient's aortic arch when the embolic protection device is in the expanded position, and wherein the filter mesh material is a fine mesh textile fabric that is adapted to conform to the ostia of the patient's aortic arch vessels when the embolic protection device is in the expanded position.

24. The embolic protection device of claim 23, wherein the wire frame comprises at least one wire hoop configured for supporting the embolic protection device within the patient's aorta when the embolic protection device is in the expanded position.

25. The embolic protection device of claim 24, wherein the wire frame encircles a periphery of the substantially flat panel of filter mesh material, and wherein a portion of the at least one wire hoop extending away from the flat panel of filter mesh material is not covered by or directly attached to the filter mesh material filter mesh material is a fine mesh.

26. The embolic protection device of claim 24, wherein the at least one wire hoop extends away from a plane of the wire frame and is configured to contact a wall of the patient's aorta to support the embolic protection device within the patient's aorta when the embolic protection device is in the expanded position.

27. The embolic protection device of claim 23, wherein the wire frame comprises a plurality of wire hoops configured for supporting the embolic protection device within the patient's aorta when the embolic protection device is in the expanded position.

28. The embolic protection device of claim 27, wherein the plurality of wire hoops extend away from a plane of the wire frame and are configured to contact a wall of the patient's aorta to support the embolic protection device within the patient's aorta when the embolic protection device is in the expanded position.

29. An embolic protection device for deployment within a patient's aorta comprising: a substantially flat panel of filter mesh material supported on a wire frame, the wire frame encircling a periphery of the substantially flat panel of filter mesh material, the wire frame comprising a plurality of wire hoops, the embolic protection device having a compressed position, wherein the embolic protection device is compressed to a small diameter for insertion into the patient's aorta, and an expanded position, wherein the embolic protection device expands to a larger size within the patient's aorta, wherein, when the embolic protection device is in the expanded position, the plurality of wire hoops extend away from the wire frame and the flat panel of filter mesh material to a deployed position configured to support the wire frame and the panel of filter mesh material within the aorta such that the filter mesh material is configured to cover ostia of sidebranch vessels connected to the patient's aorta and allow blood to enter the sidebranch vessels, but prevent embolic material from entering the sidebranch vessels, and wherein a portion of each wire hoop extending away from the flat panel of filter mesh material is not covered by or directly attached to the filter mesh material.

30. A method of providing embolic protection for sidebranch vessels connected to a patient's aortic arch, comprising:

introducing an embolic protection device into the patient's aorta, the embolic protection device comprising a wire frame supporting a substantially flat panel of flexible filter mesh material, the embolic protection device having a compressed position, wherein the embolic protection device is compressed to a small diameter for insertion into the patient's aorta;

expanding the embolic protection device to an expanded position within the patient's aorta;

covering ostia of the sidebranch vessels connected to the patient's aortic arch with the expanded embolic protection device; and allowing the panel of flexible filter mesh material to conform to the patient's aortic arch and to conform to the ostia of the sidebranch vessels connected to the patient's aortic arch;

wherein the embolic protection device allows blood to enter the sidebranch vessels, but prevents embolic material from entering the sidebranch vessels.

31. The method of claim 30, further comprising: the wire frame comprising at least one wire hoop; extending the at least one wire hoop away from the wire frame to contact a wall of the patient's aorta; and supporting the embolic protection device within the patient's aortic arch with the at least one wire hoop.

32. The method of claim 31, wherein the wire frame surrounds a periphery of the substantially flat panel of filter mesh material, and wherein a portion of the at least one wire hoop extending away from the flat panel of filter mesh material is not covered by or directly attached to the filter mesh material.

33. The method of claim 30, further comprising: the wire frame comprising a plurality of wire hoops; extending the plurality of wire hoops away from the wire frame to contact a wall of the patient's aorta; and supporting the embolic protection device within the patient's aortic arch with the plurality of wire hoops.

34. A method of providing embolic protection for sidebranch vessels connected to a patient's aortic arch comprising: introducing an embolic protection device into the patient's aorta, the embolic protection device comprising a wire frame supporting a substantially flat panel of filter mesh material, the wire frame encircling a periphery of the substantially flat panel of filter mesh material, the wire frame comprising at least one wire hoop, with the embolic protection device in a compressed position, wherein the embolic protection device is compressed to a small diameter for insertion into the patient's aorta; expanding the embolic protection device to an expanded position within the patient's aorta; covering ostia of the sidebranch vessels connected to the patient's aortic arch with the expanded embolic protection device; extending the at least one wire hoop away from the wire frame to contact a wall of the aorta, wherein a portion of the at least one wire hoop extending away from the flat panel of filter mesh material is not covered by or directly attached to the filter mesh material; and supporting the embolic protection device within the patient's aortic arch with the at least one wire hoop; wherein the embolic protection device allows blood to enter the sidebranch vessels, but prevents embolic material from entering the sidebranch vessels.

35. The method of claim 34, wherein the wire frame comprises a plurality of wire hoops, and the method comprises: extending the plurality of wire hoops away from the wire frame to contact the wall of the patient's aorta; and supporting the embolic protection device within the patient's aortic arch with the plurality of wire hoops.

* * * * *

(12) EX PARTE REEXAMINATION CERTIFICATE (10650th)
United States Patent
Belson

(10) Number: US 8,114,114 C1
(45) Certificate Issued: Jul. 7, 2015

(54) EMBOLIC PROTECTION DEVICE

(75) Inventor: Amir Belson, Cupertino, CA (US)

(73) Assignee: EMBOLINE, INC., Los Altos, CA (US)

Reexamination Request:
No. 90/013,417, Dec. 11, 2014

Reexamination Certificate for:
Patent No.: 8,114,114
Issued: Feb. 14, 2012
Appl. No.: 10/493,854
PCT Filed: Aug. 27, 2003
PCT No.: PCT/US03/26938
§ 371 (c)(1),
(2), (4) Date: Apr. 27, 2004
PCT Pub. No.: WO2004/019817
PCT Pub. Date: Mar. 11, 2004

Related U.S. Application Data

(60) Provisional application No. 60/406,492, filed on Aug. 27, 2002.

(51) Int. Cl.
*A61M 29/00* (2006.01)
*A61F 2/01* (2006.01)

(52) U.S. Cl.
CPC ............. *A61F 2/01* (2013.01); *A61F 2002/016* (2013.01)

(58) Field of Classification Search
None
See application file for complete search history.

(56) References Cited

To view the complete listing of prior art documents cited during the proceeding for Reexamination Control Number 90/013,417, please refer to the USPTO's public Patent Application Information Retrieval (PAIR) system under the Display References tab.

*Primary Examiner* — Glenn K Dawson

(57) ABSTRACT

The embolic protection device (10) has an expandable tubular structure supporting a filter mesh material (12). The embolic protection device is compressed to a small diameter for insertion into a patient's aorta, then expanded within the aorta with the filter mesh material positioned to allow blood to enter sidebranch vessels connected to the aorta and to prevent embolic material from entering the sidebranch vessels. The filter mesh material may be configured with waves or undulations (26) for increased surface area and/or with two layers of mesh material to provide additional protection against embolization and to prevent inadvertent occlusion of the sidebranch vessels.

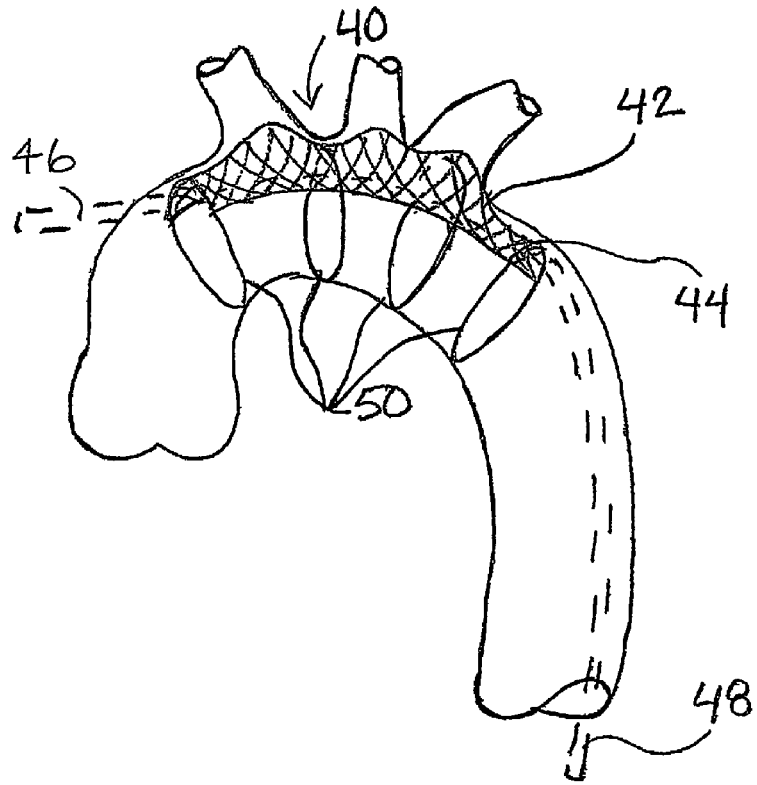

EX PARTE REEXAMINATION CERTIFICATE

NO AMENDMENTS HAVE BEEN MADE TO THE PATENT

AS A RESULT OF REEXAMINATION, IT HAS BEEN DETERMINED THAT:

The patentability of claims 1-35 is confirmed.

* * * * *